(12) United States Patent
Hoheisel et al.

(10) Patent No.: US 6,181,769 B1
(45) Date of Patent: Jan. 30, 2001

(54) X-RAY DETECTOR WITH ANATOMICALLY ADAPTED RECESS

(75) Inventors: Martin Hoheisel; Hartmut Sklebitz, both of Erlangen (DE)

(73) Assignee: Siemens Aktiengesellschaft, Munich (DE)

( * ) Notice: Under 35 U.S.C. 154(b), the term of this patent shall be extended for 0 days.

(21) Appl. No.: 09/158,060

(22) Filed: Sep. 22, 1998

(30) Foreign Application Priority Data

Oct. 1, 1997 (DE) .................................. 197 43 525

(51) Int. Cl.[7] ........................................ H05G 1/64
(52) U.S. Cl. ........................ 378/98.8; 378/189; 378/177
(58) Field of Search ....................... 430/966; 250/336.1; 378/37, 98.8, 167, 177, 189, 182

(56) References Cited

U.S. PATENT DOCUMENTS

| | | |
|---|---|---|
| 3,381,129 | 4/1968 | Duftschmid . |
| 4,341,955 | 7/1982 | Mulder et al. . |
| 4,799,094 | 1/1989 | Rougeot . |
| 4,905,269 * | 2/1990 | Mosby ............................ 378/182 |
| 5,043,582 * | 8/1991 | Cox et al. . |
| 5,313,066 | 5/1994 | Lee et al. . |
| 5,555,284 * | 9/1996 | Kishigami . |
| 5,715,292 * | 2/1998 | Sayag et al. ..................... 378/98.8 |

FOREIGN PATENT DOCUMENTS

OS 35 01 974   7/1986 (DE) .

* cited by examiner

Primary Examiner—David V. Bruce
Assistant Examiner—Pamela R. Hobden
(74) Attorney, Agent, or Firm—Schiff Hardin & Waite

(57) ABSTRACT

An x-ray detector for acquiring an x-ray image is in the form of a matrix with at least one of the sides of the amorphous silicon x-ray detector matrix having a cutout or recess with a curved contour that is adapted to the anatomy of the body part to be examined for an average patient.

8 Claims, 3 Drawing Sheets

X-RAY DETECTOR WITH ANATOMICALLY ADAPTED RECESS

BACKGROUND OF THE INVENTION

1. Field of the Invention

The present invention is directed to an x-ray detector for acquiring an x-ray image of the type composed of a scintillator which generates an optical image and an arrangement for acquiring the generated optical image.

2. Description of the Prior Art

X-ray detectors of the above general type are utilized for medical purposes in x-ray diagnostics installations.

X-ray detectors currently obtainable in the marketplace usually have a quadratic or rectangular shape. Thus, x-ray films with reinforcing or intensifier film and storage film systems have a rectangular format. The solid-state matrix detectors of cesium iodide (CsI) and amorphous silicon (a-Si) disclosed in European Application 0 189 710 and currently being developed or, as disclosed in U.S. Pat. No. 5,313,066, composed of selenium (Se) and a-Si, also have a rectangular quadratic format.

X-ray image intensifiers, by contrast, have a round structure through which x-rays enter so that a circular x-ray image is produced.

There are types of x-ray exposures wherein it is desirable to come as close as possible to the human body with the x-ray exposure system. In, for example, mammographic exposures, it is desirable to examine the tissue close to the chest wall. In thorax exposures, the neck of the patient should also be imaged. The existing x-ray exposure systems with their formats are not optimally suited for such purposes.

Heretofore, x-ray exposure systems were designed such that the x-ray-sensitive surface extends to the edge of the detector at least at one side. Thus, the spacing from the chest wall of the x-ray film in the film-foil cassette of a mammographic diagnostic installation only amounts to a few millimeters. It is possible to get that close to the chest wall of the patient at only one location.

SUMMARY OF THE INVENTION

An object of the present invention is to provide an x-ray detector of the type initially described wherein the matrix of the region serving for imaging projects as closely as possible to the body of a person under examination, so that examinations of locations that are difficult to reach are also possible.

This object is achieved by an inventively fashioned amorphours silicon x-ray detector, wherein at least one of the sides of the x-ray detector has a cutout or recess with a curved contour. As a result, the x-ray detector can be adapted optimally well to the anatomical conditions, so that it extends directly up to the body of a patient over wide areas.

It has proven advantageous for the x-ray detector to be fashioned such that the contour of the curved side adapts to the anatomy of the body part under examination in an average patient.

Inventively, the x-ray detector can have a concave cutout. The x-ray detector can be adapted to differently shaped bodies or body parts when the concave cutout is asymmetrically fashioned. The x-ray detector can thereby be fashioned such that two neighboring sides that reside at a right angle relative to one another have concave cutouts that can be provided with different contours.

It is proven advantageous for the x-ray detector to be fashioned such that at least one of the sides of the x-ray detector has a convex cutout.

Inventively, the x-ray detector can be fashioned such that one of its sides has a neck cutout.

The x-ray detector can contain a semiconductor image converter for converting an x-ray image into an electrical signal sequence, composed of radiation-sensitive cells arranged in a matrix and driver circuits for driving and reading out the cells that are connected to the cells via lines, with all cells being connected to a driver circuit displaced opposite the cutout.

DESCRIPTION OF THE PREFERRED EMBODIMENTS

Figure 1:
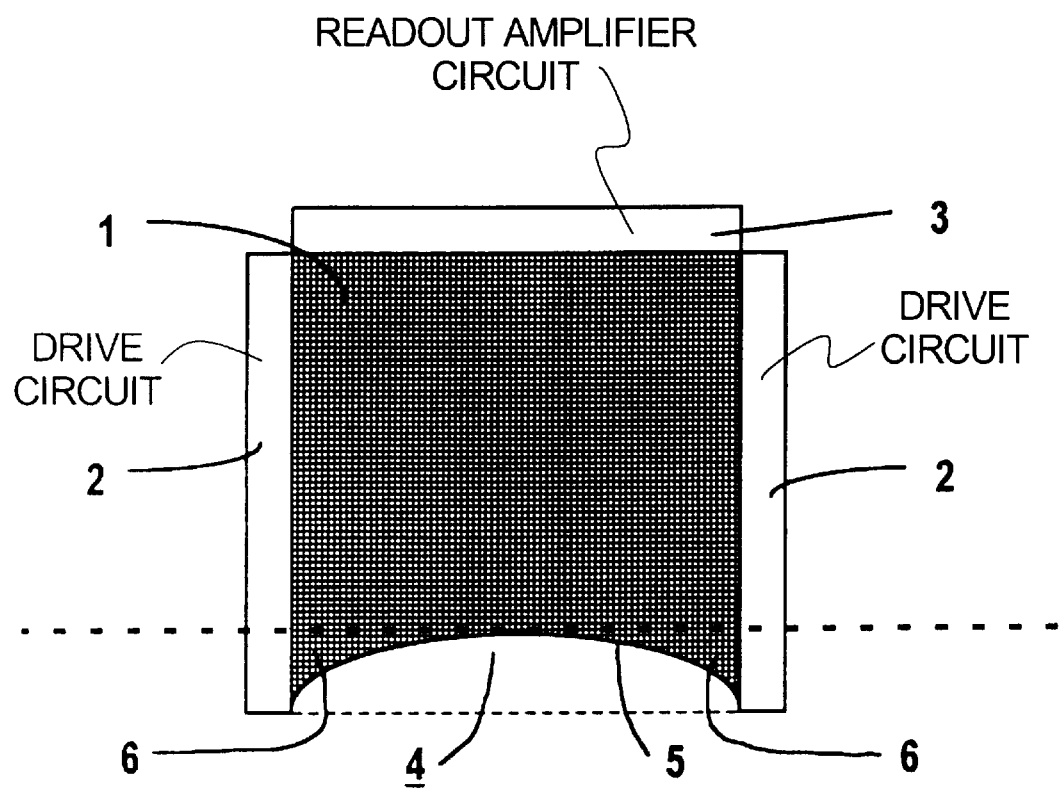
FIG. 1 shows an inventive matrix detector with a concavely curved cutout.

A first embodiment of the inventive matrix detector 1 is shown in FIG. 1. Photodiodes, switch elements, for example thin-film transistors or switching diodes, and interconnects are applied on a rectangular glass substrate with known thin-film deposition techniques and photolithographic structuring such that they form a matrix-shaped array of small n rows and small m columns of picture elements. The photodiodes are thereby advantageously manufactured of amorphous silicon (a-Si).

The interconnects for the drive of the individual picture elements lead to two sides of the rectangular matrix detector 1 and are connected at these sides to the drive circuits 2, via which the switches of the individual picture elements are supplied with voltage pulses in a known way. The generated signal charges are readout from the picture elements as electrical signals via interconnects, these signals are intensified by readout amplifier circuits 3 arranged a third side of the matrix detector 1, and are supplied for further processing.

An inventive cutout 4 with a curved contour is provided at the fourth side of the matrix detector 1. This contour, for example, can be concave. This contour of the curved cutout 4 can be adapted to the anatomy of the body part to be investigated for an average patient.

For manufacturing the curved cutout 4, a sequence of small holes is generated in the glass surface with a laser beam along a desired cut edge 5, for example by laser perforation with an excimer laser. These holes can be through holes or blind holes. The holes have, for example, a diameter of 50 $\mu$m and a spacing of 100 $\mu$m and a depth (if not through holes) that amounts to half the thickness of the glass substrate. The holes must completely separate the interconnects, photodiodes and switches so that no shorts between neighboring interconnects can occur during this process step. Subsequently, the glass substrate that has been perforated along the predetermined cut edge 5 is very precisely broken.

As can also be seen from FIG. 1, the drive circuits 2 are arranged at two sides of the matrix 1, so that it is assured that each picture element even in the side regions 6 to the side of the cut edge 5 is connected to a drive circuit 2.

The substrate produced in this way is vapor-deposited with cesium iodide in order to make it sensitive to x-ray radiation. Alternatively, the substrate can already be provided with a scintillator before the shaping, which can be subsequently broken together with the substrate to form the cutout 4.

The advantage of such a manufacturing method is that a decision can be made regarding the shape that the rectangular sensor should have after the manufacture of the rectangular sensor. Proceeding from a single basic substrate design, it is thus possible to produce a rectangular detector and a number of differently shaped detectors, so that a considerable cost-saving is achieved.

In a further manufacturing method, the fracture line that is provided is already taken into consideration in the photolithographic structuring. The interconnects are thereby made to terminate short of the location at which the cut edge 5 of the glass substrate will subsequently be made. As a result of this arrangement, it is already possible to test the sensors before the shaping. The risk of influencing the electrical properties by the laser process is lower with this procedure, however, it is limited producing one specific form.

In a third manufacturing embodiment, the detector is not vapor-deposited with cesium iodide. instead, the individual picture elements are constructed of switches in thin-film technique above which a semiconductor layer is arranged for direct absorption of x-radiation. The absorbed x-ray quanta generate electrical charges in this semiconductor layer. Such a layer, for example, can be composed of selenium. The structuring of such a detector then ensues analogously to the above-described manufacturing methods.

Gadolinium oxisulfide or some other suitable material can be employed as scintillator material instead of cesium iodide.

In other embodiments, for example, the terminals of the drive circuits 2 and readout amplifier circuits 3 can be interchanged.

Figure 2:
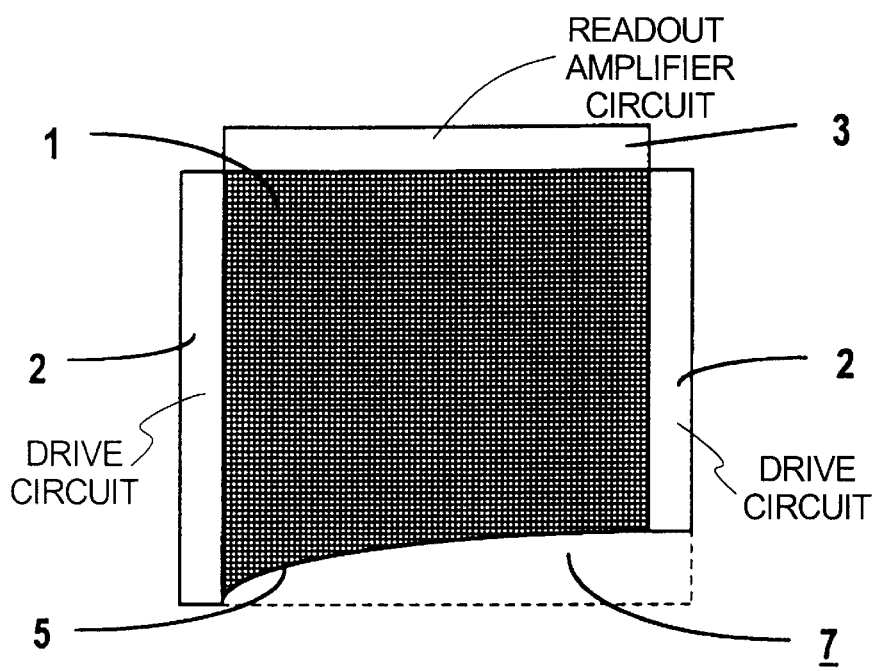
FIG. 2 shows an inventive matrix detector with an asymmetrical cutout.

As shown in FIG. 2, the shape of the detector can be inventively asymmetrical, such as an asymmetrical, concave cutout 7.

Figure 3:
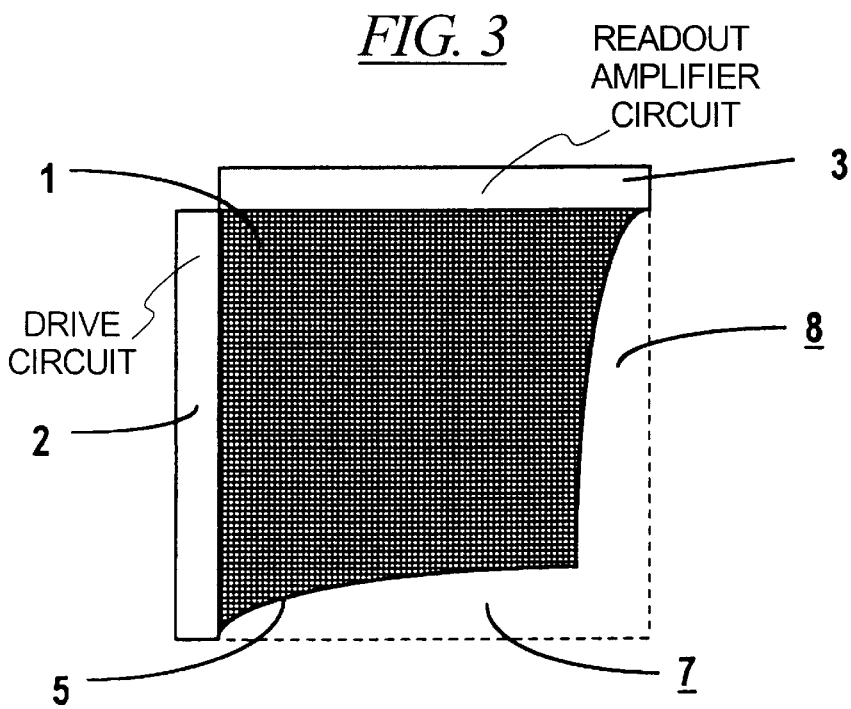
FIG. 3 shows an inventive matrix detector with two asymmetrical, concave cutouts.
Figure 4:
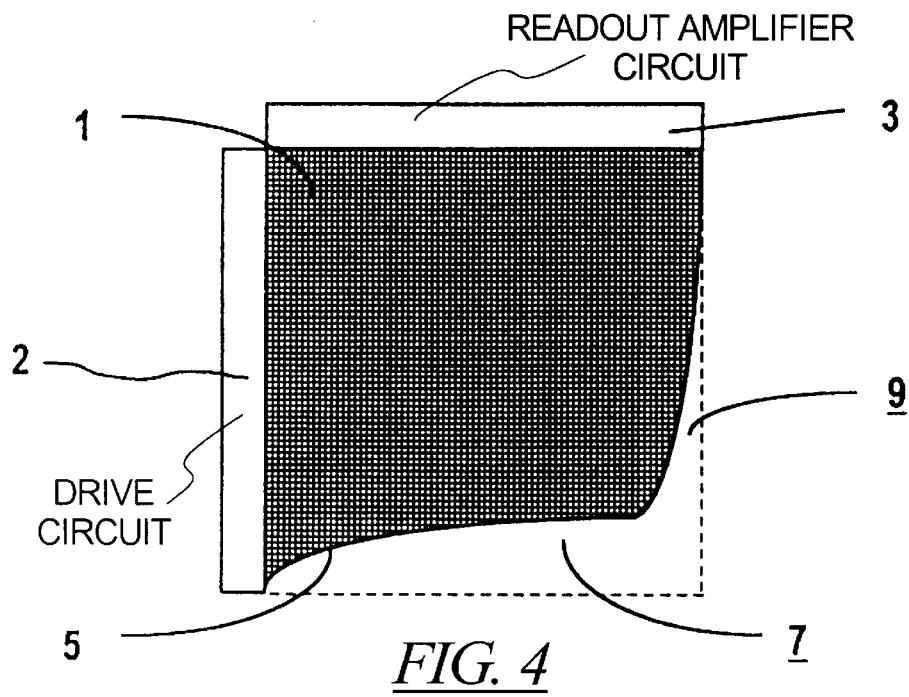
FIG. 4 shows an inventive matrix detector with a concavely curved cutout and a convexly curved cutout.
Figure 5:
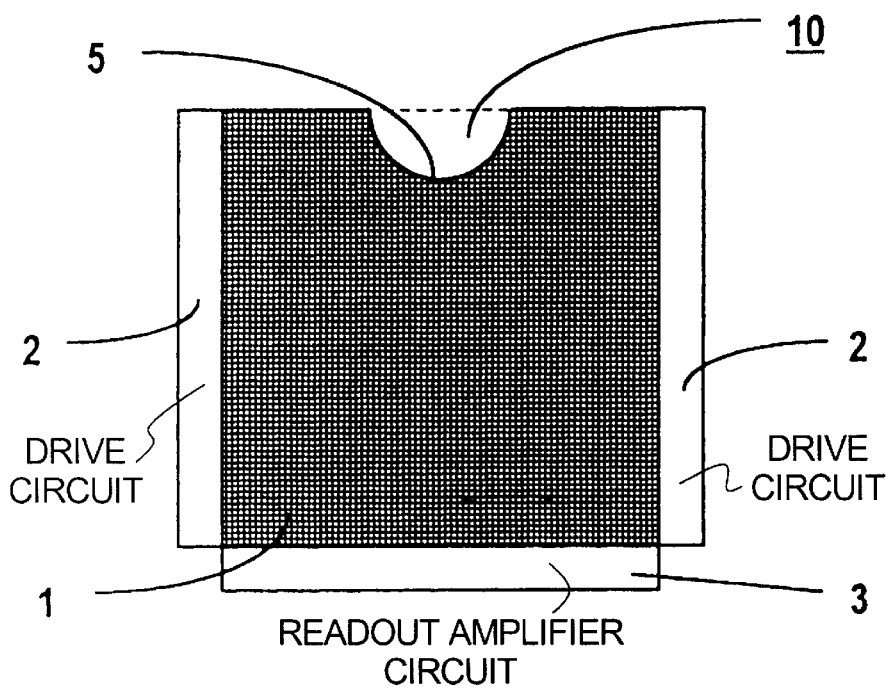
FIG. 5 shows an inventive matrix detector with a semicircular neck cutout.

The inventive principle can still be employed when the drive lines are conducted such that drive circuits 2 are needed at only one side of the detector. The matrix detector 1 can then also be shaped concavely at two neighboring sides, as can be seen from FIG. 3. As a result of the two asymmetrical, concave cutouts 7 and 8, which can be differently fashioned, an adaptation to a large variety of body shapes, even given different exposure directions, is possible. Alternatively, the matrix detector 1 can have a convex cutout 9 as shown in FIG. 4.

Specifically for thorax exposures, only a part of one side of the matrix detector 1 is provided with such a cut edge 5, arranged centrally in this side, so that a semicircular neck cutout 10 shown in FIG. 6 is produced.

The format of x-ray detectors was conventionally limited to the geometrical shapes of "rectangle" or "circle". This limitation is eliminated with this inventive fashioning of the x-ray detector, so that new x-ray systems that can be adapted better to human anatomy can be realized.

Particularly in mammography, such a concavely shaped x-ray detector makes it possible to considerably improve the imaging in the immediate proximity of the chest wall. This is of substantial diagnostic use.

As a result of the inventive arrangement of the terminal lines of the matrix detector 1 at only three sides, the curved cutout 4, 7 or 10 can be applied at the fourth side. The drive circuits 2 are arranged at two sides, so that the side regions can also be driven. The signal charges that are generated are amplified by readout amplifier circuits 3 at the third side. No circuits are provided at the fourth side, but this side has a concave cutout 4, allowing the shape of the cutout can be adapted to the body of an average patient in conformity with the respective application.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray detector for acquiring an x-ray image, comprising:

an amorphous silicon radiation detector having a plurality of sides, with at least one of said sides having a recess therein with a curved contour.

2. An x-ray detector as claimed in claim 1 wherein said curved contour of said at least one of said sides of said radiation detector is anatomically adapted to a body part of an average patient.

3. An x-ray detector as claimed in claim 1 wherein said curved contour of said at least one of said sides comprises a concave contour.

4. An x-ray detector as claimed in claim 1 wherein said curved contour in said at least one of said sides is asymmetrical.

5. An x-ray detector as claimed in claim 1 wherein said plurality of sides of said radiation detector include two neighboring sides, and wherein each of said two neighboring sides has a recess with a curved contour therein.

6. An x-ray detector as claimed in claim 1 wherein said curved contour of said at least one of said sides of said radiation detector comprises a convex contour.

7. An x-ray detector as claimed in claim 1 wherein said curved contour in said at least one of said sides of said radiation detector comprises a contour anatomically adapted to a human neck.

8. An x-ray detector as claimed in claim 1 wherein said radiation detector comprises a semiconductor image converter for converting an incident x-ray image into a plurality of electrical signals, said converter comprising a plurality of radiation-sensitive cells and driver circuits arranged in a matrix, said driver circuit being connected to all cells in said matrix and being disposed at a side of said radiation detector opposite said at least one of said sides containing said recess.

\* \* \* \* \*